US00PP12551P2

(12) United States Plant Patent
Rankin

(10) Patent No.: US PP12,551 P2
(45) Date of Patent: Apr. 16, 2002

(54) APPLE TREE NAMED 'RANKIN RED'

(75) Inventor: Edward W. Rankin, Gettysburg, PA (US)

(73) Assignee: Twin Springs Fruit Farm, Inc., Ortanna, PA (US)

( * ) Notice: Subject to any disclaimer, the term of this patent is extended or adjusted under 35 U.S.C. 154(b) by 0 days.

(21) Appl. No.: 09/729,500

(22) Filed: Dec. 4, 2000

(51) Int. Cl.[7] ..... A01H 5/00
(52) U.S. Cl. ..... Plt./161

(58) Field of Search ..... Plt./161, 168

*Primary Examiner*—Bruce R. Campell
*Assistant Examiner*—Susan B. McCormick
(74) *Attorney, Agent, or Firm*—James A. Lucas; Driggs, Lucas, Brubaker & Hogg Co., L.P.A.

(57) ABSTRACT

A new and distinct strain of apple, designated 'Rankin Red', originated as a limb sport on a 'Yataka' tree. It matures 5 days earlier than 'Yataka' and 5 weeks earlier than 'Fuji.' Other significant improvements over 'Yataka' and 'Fuji' include increased color intensity, a higher percentage of red color, greater color uniformity, less russet and a smoother finish.

3 Drawing Sheets

BACKGROUND OF THE INVENTION

This invention relates to apple trees and, more specifically, to an apple tree referred to as a strain , or bud mutation, of *Malus domestica* Borkh. 'Yataka' U.S. Plant Pat. No. 7,001).

I discovered this new and unique strain of apple tree as a limb sport on 'Yakata' in a cultivated area near Orrtanna, Pa. The tree of this invention produces a fruit of attractive commercial value, with smoother finish and brighter, more uniform color than 'Yataka.' Harvest period is 5 days earlier than 'Yataka' and 5 weeks earlier than 'Fuji' (unpatented parent of 'Yataka').

This new strain of apple tree was asexually reproduced by grafting near Aspers, Pa., and such reproduction has shown this new strain to come true in two successive generations. This propagation of the new strain by grafting under standard controlled conditions clearly discloses the continued maintenance of the characteristics described herein which distinguish this new strain from the parent cultivar.

SUMMARY OF THE INVENTION

This new and distinctive strain of apple tree produces a fruit with solid red color covering 70 to 90% of the fruit surface, compared to 30 to 50% with 'Yataka.' Color intensity, color uniformity and finish also are superior to 'Yataka.'

DESCRIPTION OF THE DRAWINGS

This new strain of apple tree is illustrated by the accompanying photographic drawings, depicting the plant by the best possible color representation using color photography.

FIG. 1: Close-up of 3 specimens of fruit on the new tree in different orientations to reflect the uniform size, shape and characteristics color and finish. Note uniformity of color among fruits.

FIG. 2: At center, 2 whole specimens of fruit (one shown from the stem end and one from the calyx end) and 1 partially dissected specimen showing seed cavity and flesh color. At either side of fruit, terminal shoots from a 3-year-old tree, showing current season's growth, leaves, leaf arrangement and leaf spacing.

FIG. 3: Second generation, 3-year-old tree, showing canopy form and fruit density.

BOTANICAL DESCRIPTION OF THE PLANT

All color references below are measured against The Royal Horticultural Society Colour Chart. Colors are approximate as color depends on horticultural practices such as light level and fertilization rate, among others.

Parentage: Limb sport on a 'Yataka' tree. Asexually reproduced by bud grafting.

Tree: 5½ ft tall by 4 ft wide and 5 to 10 lbs fruit per tree, on M.26 rootstock, at 3 years age, near Aspers, Pa. Upright-spreading tree of medium vigor, hardy, spur bearer, productive, should be thinned early and adequately for regular bearing.

*Trunk.*—Medium girth, moderately rough, gray, RHS 201B, observed diameter 1½" at 10" height above soil level (typical for a tree of this age).

Branches: Medium thick, ⅜" at junction with trunk (typical for a tree of this age) smooth, medium branching, 60 degree crotch angles, brown, RHS 200D.

*Lenticels.*—Numerous, small,length — ¼"; width — 1/16", color-greyed-orange, RHS 165C.

Leaves:

*Length.*—2⅞ inches.

*Width.*—1⅝ inches. Shape ovate, Texture smooth, Small width, medium length, flat surface, upward folding, broadly acute, medium thick, dark green, RHS 137B for upper foliage surface, RHS 137D for lower surface.

*Margins.*—Finely serrate.

*Veins.*—Light green RHS 138D, venation pattern ribbed, reticulate.

*Petioles.*—Length ⅞ inch, moderately long, medium thick. Color — light green, RHS 138D; Diameter — 1/16".

*Stipules.*—Number — 2, length — 5/16", color— green RHS 137B.

Flowers:

*Dates of first and full blossoms.*—April 21 and 26, near Aspers, Pa. Early-midseason bloom period.

*Size.*—Medium, 1 5/16" in diameter by 3/16" deep.

*Color.*—White (RHS 155A both surfaces) to pale red purple, (RHS 62D both surfaces).

*Petals.*—Number, 5; shape, ovoid; apex-rounded; base-rounded; margin-entire; texture smooth.

*Pollination.*—Low self-fertilization, needs pollinizer with overlapping bloom period such as 'Jonathan' or 'Gala.'

Fruit:

*Maturity when described.*—Ripe.

*Date.*—Sep. 11, 2000 (matures 5 days earlier than 'Yataka' and 5 weeks earlier than 'Fuji').

*Uniformity of maturity.*—Excellent.

*Size.*—Uniformly large.

*Diameter.*—3 inches.

*Length.*—2 7/8 inches.

*Form.*—Rounded, slightly longer than wide, regular cross-section.

*Cavity.*—Symmetrical, flaring, depth 1/4 inch, breadth 3/4 inch, green-russet (yellow-greenish RHS 151A) markings.

*Stem.*—Medium, slightly pubescent, length 3/4 inch, diameter 1/8"; color greyed orange RHS 172D 0 to 2 bracts per stem.

*Basin.*—Depth 1/4 inch, breadth 7/8 inch.

*Calyx.*—Half-open, sepals erect, diameter 3/8 inch.

*Skin.*—Medium thick, smoother than 'Yataka', glossy.

*Lenticels.*—Medium size, moderate number, circular, cream white, RHS 155D or light yellow green, RHS 151C, scattered over most of surface.

*Russet.*—Slight, some raised lenticels (significantly less than 'Yataka').

*Ground color.*—Yellow-green, RHS 154D.

*Color markings.*—Solid red over 70 to 90% of surface with slight stripes, bright, deep pink-red, RHS 185B (as contrasted to 30 to 50% striped, dull red, RHS 185C 'Yataka').

*Bloom.*—Scant.

*Scarfskin.*—Wanting.

*General color effect.*—Bright pink red (RHS 185B), more intense than 'Yataka.'

*Flesh.*—Juicy, creamy, RHS 159D, not easily bruised.

*Texture.*—Firm, coarse, crisp.

*Flavor.*—Sweet.

*Aroma.*—Mild.

*Eating quality.*—Best, 12 to 16% soluble solids, 16 to 18 lbs firmness at harvest maturity, watercore in well-matured fruit.

*Core.*—Median (between calyx and stem ends).

*Carpellary area.*—Distinct.

*Core lines.*—Meeting.

*Calyx tube.*—Cone-shaped.

*Depth of tube.*—3/8 inch.

*Axis.*—Axile.

*Seed cells.*—Mostly closed.

*Cell walls.*—Thin, lanceolate in longitudinal section, narrow to medium in cross-section (length 3/8 inch, breadth 1/8inch), surface tufted.

Seeds: Number perfect 10, largest number in one cell 2, length 3/8 inch, breadth 3/16 inch, form acute.

*Color.*—Greyed-orange RHS 166B.

Uses: Excellent for dessert or processing markets.

Keeping quality: Excellent in regular or controlled atmosphere storage, 180 days in regular atmosphere storage, good shelf life at room temperature, maintains firmness.

Resistance to insects: Medium, incidence similar to that of other cultivars Gala, Empire, Jonagold in planting.

Resistance to diseases: Medium, incidence similar to that of other cultivars Gala, Empire, Jonagold in planting. Winter hardy; drought and heat tolerant; moderately susceptible to sunburn.

What is claimed is:

1. A new and distinct strain of apple tree, as illustrated and described, characterized by early maturity, bright red color and smooth finish.

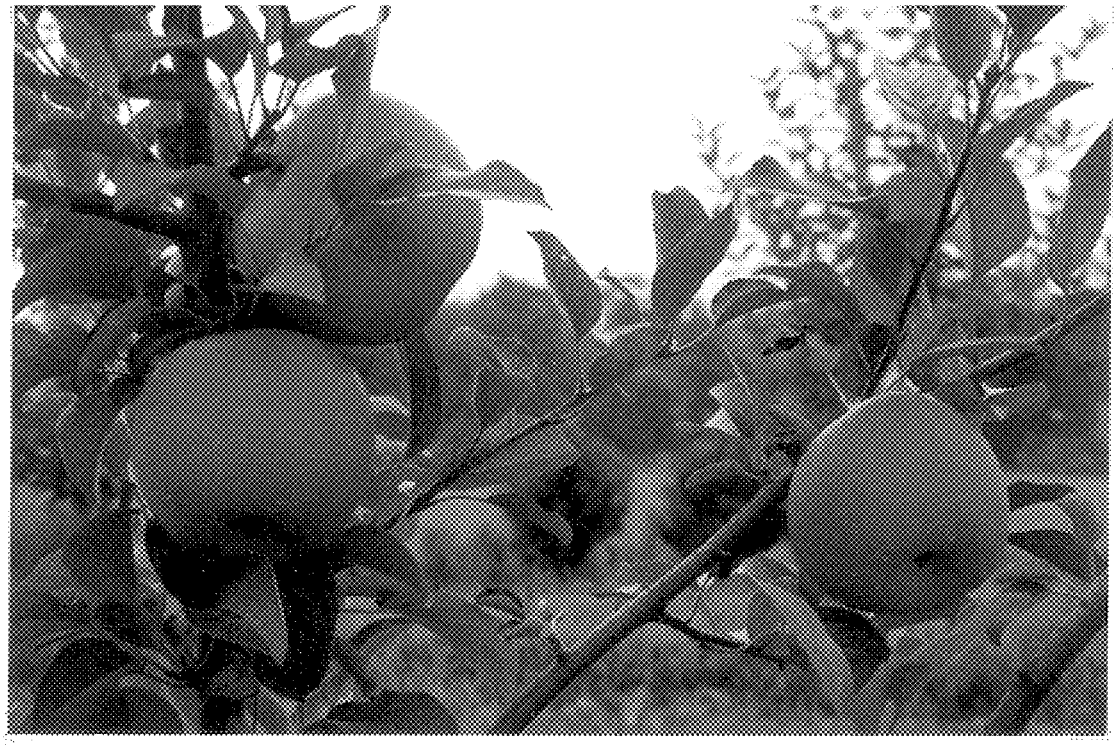

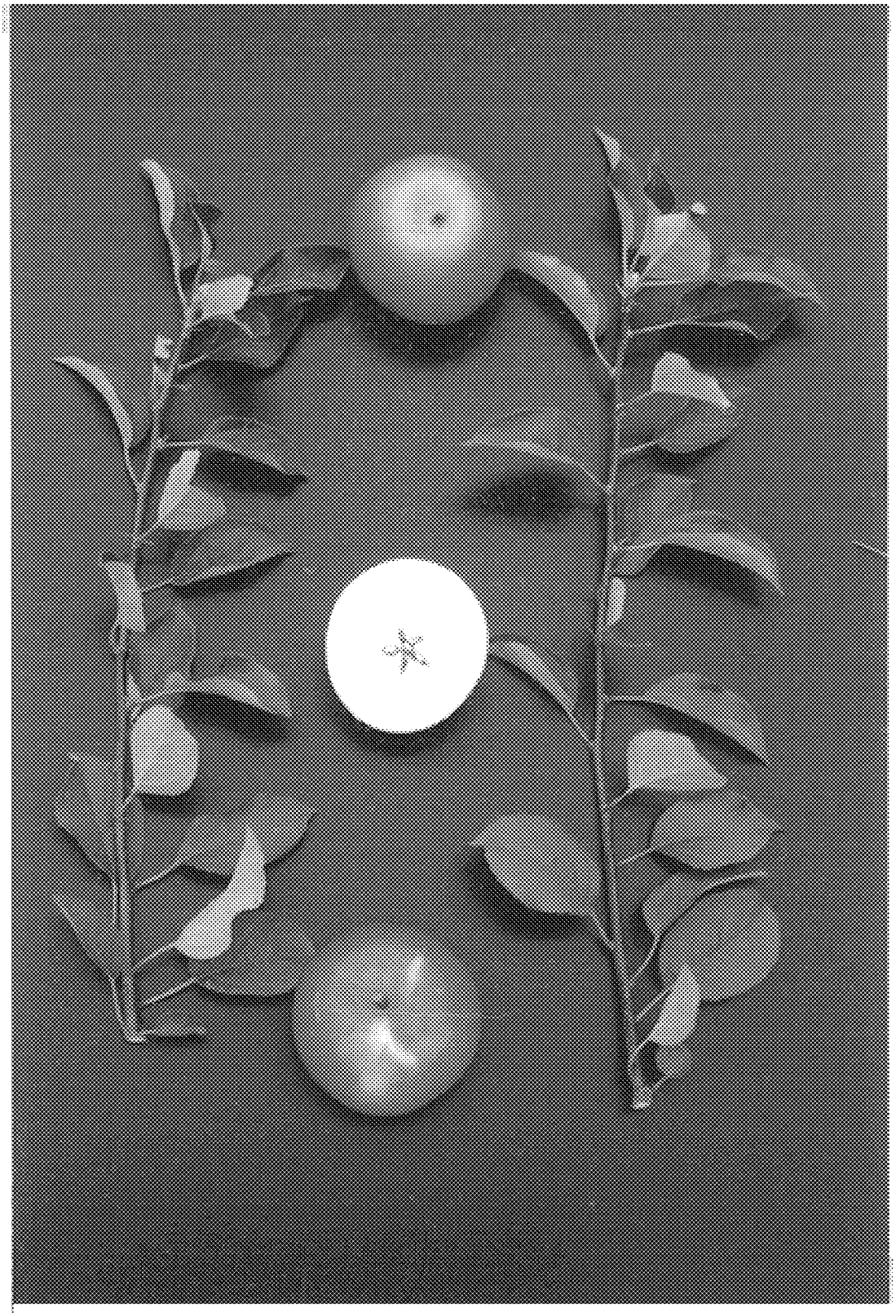

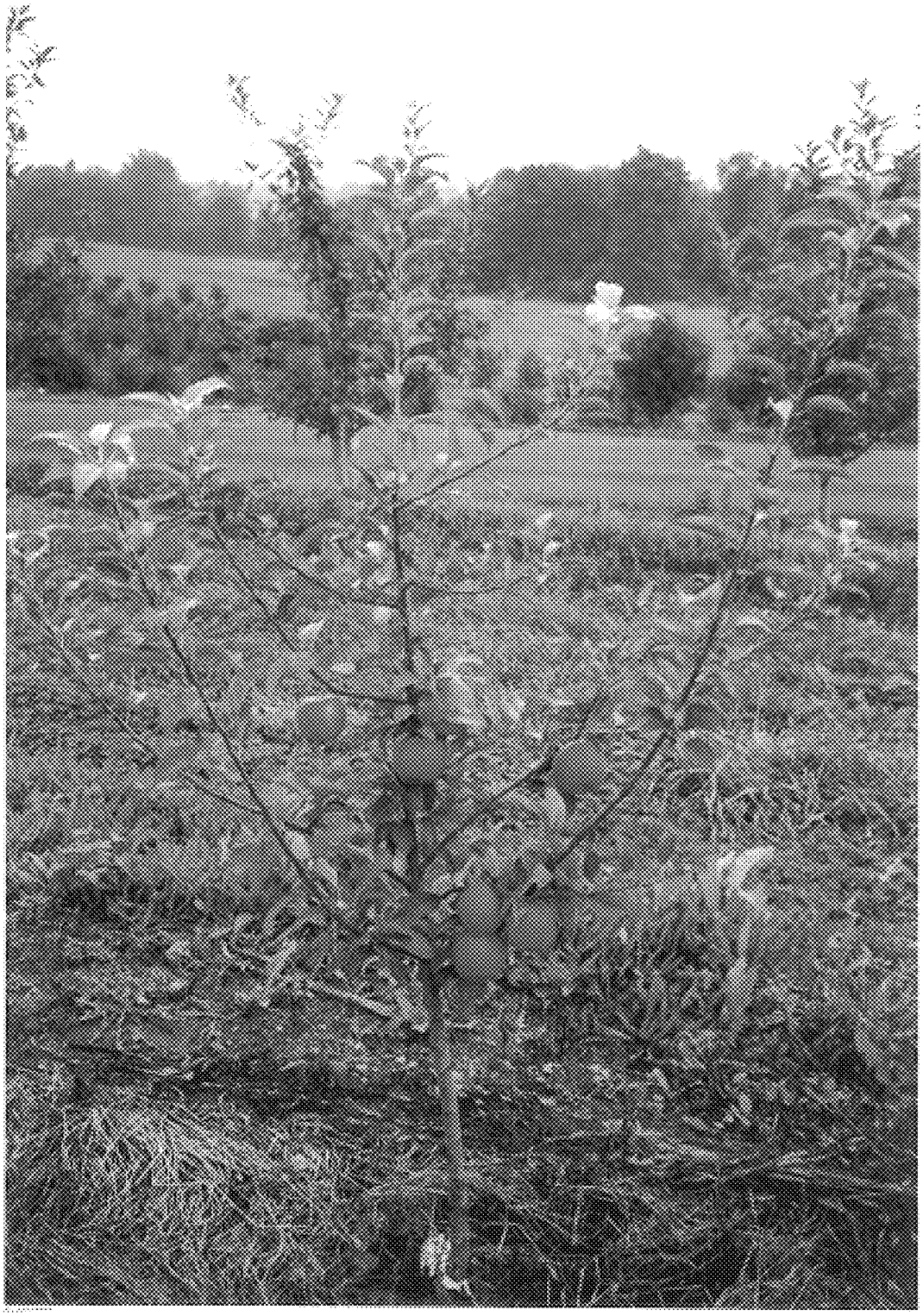

* * * * *